United States Patent
Seki (10) Patent No.: US 12,298,303 B2
(45) Date of Patent: May 13, 2025

(54) TEST DEVICE, TEST KIT, AND TEST METHOD

(71) Applicant: ICST CORPORATION, Saitama (JP)

(72) Inventor: Masaaki Seki, Saitama (JP)

(73) Assignee: ICST CORPORATION (JP)

( * ) Notice: Subject to any disclaimer, the term of this patent is extended or adjusted under 35 U.S.C. 154(b) by 0 days.

(21) Appl. No.: 17/918,420

(22) PCT Filed: Dec. 1, 2021

(86) PCT No.: PCT/JP2021/044116
§ 371 (c)(1),
(2) Date: Oct. 12, 2022

(87) PCT Pub. No.: WO2022/168418
PCT Pub. Date: Aug. 11, 2022

(65) Prior Publication Data
US 2023/0120219 A1    Apr. 20, 2023

(30) Foreign Application Priority Data
Feb. 4, 2021 (JP) .................................. 2021-016544

(51) Int. Cl.
*G01N 33/569* (2006.01)
*G01N 21/01* (2006.01)
*G01N 33/53* (2006.01)
*G01N 33/68* (2006.01)

(52) U.S. Cl.
CPC ....... *G01N 33/56983* (2013.01); *G01N 21/01* (2013.01); *G01N 33/5302* (2013.01); *G01N 33/6854* (2013.01); *G01N 2021/0106* (2013.01); *G01N 2333/165* (2013.01)

(58) Field of Classification Search
CPC ......... G01N 33/56983; G01N 33/6854; G01N 2333/165; G01N 33/5302
See application file for complete search history.

(56) References Cited

U.S. PATENT DOCUMENTS

| | | |
|---|---|---|
| 7,074,555 B2 | 7/2006 | Esty et al. |
| 7,201,903 B2 | 4/2007 | Groat et al. |
| 7,284,432 B2 | 10/2007 | Hock et al. |
| 7,611,717 B2 | 11/2009 | Murtaugh et al. |
| 7,776,546 B2 | 8/2010 | Groat et al. |
| 8,399,187 B2 | 3/2013 | Murtaugh et al. |
| 8,638,441 B2 | 1/2014 | Egan et al. |
| 9,222,875 B2 | 12/2015 | Egan et al. |
| 9,567,375 B2 | 2/2017 | Luo et al. |
| 2005/0058992 A1 | 3/2005 | Groat et al. |
| 2005/0058993 A1 | 3/2005 | Groat et al. |
| 2005/0244814 A1 | 11/2005 | Esty et al. |
| 2006/0188519 A1 | 8/2006 | Cheung et al. |
| 2006/0219536 A1 | 10/2006 | Hock et al. |
| 2007/0003570 A1 | 1/2007 | Murtaugh et al. |
| 2008/0017486 A1 | 1/2008 | Francis et al. |
| 2008/0268426 A1 | 10/2008 | Murtaugh et al. |
| 2010/0035276 A1 | 2/2010 | Murtaugh et al. |
| 2010/0136055 A1 | 6/2010 | Luo et al. |
| 2010/0315644 A1 | 12/2010 | Egan et al. |
| 2011/0189651 A1 | 8/2011 | Groat et al. |
| 2014/0343860 A1 | 11/2014 | Egan et al. |
| 2017/0151321 A1 | 6/2017 | Luo et al. |
| 2019/0240311 A1 | 8/2019 | Reimann et al. |
| 2020/0378957 A1* | 12/2020 | Azpiroz .............. G01N 33/536 |
| 2021/0190797 A1 | 6/2021 | Messing et al. |

FOREIGN PATENT DOCUMENTS

| | | |
|---|---|---|
| CN | 102483399 A | 5/2012 |
| CN | 102818898 A | 12/2012 |
| CN | 102965348 A | 3/2013 |
| CN | 206756849 U | 12/2017 |

(Continued)

OTHER PUBLICATIONS

Cavalera S et al. A multi-target lateral flow immunoassay enabling the specific and sensitive detection of total antibodies to SARS COV-2. Talanta. Feb. 1, 2021;223(Pt 1):121 (Year: 2021).*
Li Z et al. Development and clinical application of a rapid IgM-IgG combined antibody test for SARS-CoV-2 infection diagnosis. J Med Virol. Sep. 2020 (Year: 2020).*
Anfossi L, Di Nardo F, Cavalera S, Giovannoli C, Baggiani C. Multiplex Lateral Flow Immunoassay: An Overview of Strategies towards High-throughput Point-of-Need Testing. Biosensors (Basel). Dec. 26, 2018;9(1):2. (Year: 2018).*
Anna MacDonald—COVID-19 Antibody Testing_ S vs. N Protein _ Technology Networks—2020 (Year: 2020).*

(Continued)

*Primary Examiner* — Janet L Andres
*Assistant Examiner* — Ruixue Wang
(74) *Attorney, Agent, or Firm* — Harness, Dickey & Pierce, P.L.C.

(57) ABSTRACT

A test device by immunochromatography comprises a case including a dropping window for a specimen and a detection window, and a test piece in the case. The test piece includes first and second detection portions, and a dropping area common to the first and second detection portions. When the specimen is dropped on the dropping area through the dropping window, the specimen migrates downstream and the same specimen reaches the first and second detection portions. The first detection portion traps a complex of a first labeled body and a first antibody contained in the specimen. The second detection portion traps a complex of a second labeled body and a second antibody contained in the specimen. The first antibody is produced by vaccination or infection with a predetermined virus. The second antibody is produced by infection with the virus. Thus, a test result from each of the first and second detection portions, both visually observed through the detection window, can be determined in parallel and at the same time.

7 Claims, 6 Drawing Sheets

(56) References Cited

FOREIGN PATENT DOCUMENTS

| CN | 110058010 A | 7/2019 |
|---|---|---|
| CN | 111999492 A | 11/2020 |
| EP | 3734286 A1 | 11/2020 |
| JP | 2008-503727 A | 2/2008 |
| JP | 2012-523568 A | 10/2012 |
| JP | 6217141 B2 | 10/2017 |
| JP | 2019-506850 A | 3/2019 |
| JP | 2021-167805 A | 10/2021 |
| WO | 2021-072501 A1 | 4/2021 |

OTHER PUBLICATIONS

FDA News Release: FDA Takes Key Action in Fight Against COVID-19 By Issuing Emergency Use Authorization for First COVID-19 Vaccine. Dec. 11, 2020. (Year: 2020).*

International Search Report (English and Japanese) issued in PCT/JP2021/044116, mailed Jan. 25, 2022; ISA/JP (7 pages).

Discussion of SARSCoV-2 antibody test reagent for novel coronavirus infection(COVID-19)—association between properties depending on difference in original species of antigens and antigenisotypes Oct. 25, 2020, vol. 69, No. 4, p. 554-561, ISSN 0915-8669 (25 pages).

Okba, N. M. A. et al., Severe Acute Respiratory Syndrome Coronavirus 2—Specific Antibody Responses in Coronavirus Disease Patients, Emerging Infectious Diseases, Jul. 2020, vol. 26, No. 7, p. 1478-1488, ISSN 1080-6040 (11 pages).

Communication pursuant to Article 94(3) EPC issued in the corresponding European Patent Application No. 21924803.6; dated Mar. 11, 2024 (total 7 pages).

European Search Report issued in the corresponding European Patent Application No. 21924803.6; dated Feb. 27, 2024 (total 4 pages).

Jhong-Lin Wu, et al. "Four point-of-care lateral flow immunoassays for diagnosis of COVID-19 and for assessing dynamics of antibody responses to SARD-CoV-2"; Journal of Infection 81; Year 2020; pp. 435-442 (total 8 pages).

Lilit Grigoryan, et al. "The immunology of SARS-CoV-2 infections and vaccines"; Seminars in Immunology; vol. 50; Year 2020; pp. 1-16 (total 16 pages).

Rafael R. de Assis, et al. Analysis of SARS-CoV-2 Antibodies in COVID-19 Convalescent Blood using a Coronavirus Antigen Microarray; May 8, 2020; pp. 1-22 (total 22 pages).

Third Office Action issued in the corresponding Australian Patent Application No. 2021426144; dated Aug. 2, 2024 (total 4 pages).

Fourth Office Action issued in the corresponding Australian Patent Application No. 2021426144; dated Aug. 7, 2024 (total 4 pages).

* cited by examiner

S : SPECIMEN

LG : LABELED ANTIGEN
(S1/RBD LABELED ANTIGEN or NP LABELLED ANTIGEN)

LB : LABELED ANTIBODY LB1 or LB2

AB : S1/RBD-IgG ANTIBODY or NP-IgG ANTIBODY

IC : FIRST IMMUNE COMPLEX IC1 or
SECOND IMMUNE COMPLEX IC2

T : CAPTURE ANTIBODY T1 or T2

C : CONTROL ANTIBODY C1 or C2

TEST DEVICE, TEST KIT, AND TEST METHOD

CROSS REFERENCE TO RELATED APPLICATIONS

This application is a U.S. National Phase Application under 35 U.S.C. 371 of International Application No. PCT/JP2021/044116, filed on Dec. 1, 2021, which claims priority to Japanese Patent Application No. 2021-016544, filed on Feb. 4, 2021. The entire disclosures of the above applications are expressly incorporated by reference herein.

BACKGROUND

Technical Field

The present invention relates to a test device, a test kit, and a test method capable of antibody test.

Related Art

A conventionally known test device for performing an immunoassay is a test device employing immunochromatography.

Immunochromatography is an immunoassay that employs a property (capillary action) in which a specimen slowly flows on a porous test piece such as a cellulose membrane while dissolving a reagent therein. By using this property in an immunochromatographic test device, antigens (or antibodies) in the specimen migrate on a cellulose membrane while forming immune complexes with antibodies (or antigens) (labeled antibodies (or antigens)) labeled with metal colloid or the like previously prepared at a dropping portion on which the specimen is dropped. Subsequently, the immune complexes are trapped on capture antibodies (or antigens) previously prepared on the cellulose membrane, and colored, and finally the colored state is visually observed for determination. Immunochromatographic test devices have been adopted for diagnosis of pregnancy, influenza diagnosis, and the like.

A known example of an immunochromatographic test device is a test device or the like in which a test piece is enclosed in a rectangular case. The test piece contains previously immobilized labeled antibodies and capture antibodies, and the case includes a dropping window on which a specimen is dropped and a detection window through which the state of the test piece is visually observed (for example, see Japanese Patent No. 6217141).

Currently, a method for detecting IgG antibodies or IgM antibodies that are types of immunoglobulin in blood and that specifically react with a nucleocapsid protein (hereinafter referred to as "N antigen") and a spike protein (hereinafter referred to as "S antigen") of virus (SARS-CoV-2) causing novel coronavirus infection (COVID-19) is established.

As a simple and quick test device for determining the presence or absence of a history of novel coronavirus infection, a kit capable of measuring IgG antibodies and/or IgM antibodies in human whole blood, serum, or plasma by immunochromatography is also increasingly used.

For the antibody test devices, the labeled antigen in the test piece is the S antigen alone, the N antigen alone, or the S antigen and the N antigen together or the like. To trap an immune complex formed by binding the target antibody (for example, IgG antibody) in the specimen to the labeled antigen, the test piece includes a line (capture antibody line) to which the antibody (capture antibody, or anti-IgG antibody) is applied.

The S antigen and the N antigen are proteins of the SARS-CoV-2 virus (hereinafter referred to as novel coronavirus). Therefore, when it is possible to detect (trap) an immune complex formed by binding the antibody in the specimen to the S antigen or the N antigen on the capture antibody line, the presence or absence of a history of infection with the virus can be determined.

However, the conventional test device by immunochromatography (hereinafter referred to as "immunochromatographic test device") has difficulty in performing fractionated determination.

Specifically, the conventional immunochromatographic test device has a problem in which it cannot determine whether an antibody (neutralizing antibody, for example, IgG antibody) having a neutralization effect of reducing the infectivity of a predetermined virus (for example, novel coronavirus) is produced by natural infection or by vaccination.

It is known that an antibody that neutralizes the novel coronavirus targets a spike protein (S antigen) necessary for entrance into human cells and prevents infection by the virus. Thus, research and development of vaccine capable of producing an antibody (IgG antibody, and the like) to target (capable of binding to) the S antigen have been advanced.

When the use of a vaccine expands, it is desirable to determine the efficacy of the vaccination quickly and simply. Here, the conventional immunochromatographic test device can also detect the presence of IgG antibody (functioning as a neutralizing antibody) capable of binding to the S antigen which can be used as the labeled antigen in the test piece.

However, the IgG antibody having such a neutralization effect is produced not only by vaccination but also by viral infection (natural infection). Specifically, the immunochromatographic test device has a problem in which the test piece containing the S antigen used as the labeled antigen can detect the neutralizing antibody (for example, IgG antibody) in the specimen, but cannot determine whether the antibody is produced by vaccination or natural infection.

In a case of using both the S antigen and the N antigen as the labeled antigen in the test piece of the conventional immunochromatographic test device, the same problem occurs. In other words, an immune complex (one type of antibody) that binds to the S antigen or the N antigen is trapped on the capture antibody line as described above. In this case, when the capture antibody line is colored, the immunochromatographic test device can only determine whether the specimen contains at least the antibody (IgG antibody functioning as the neutralizing antibody) to trap the S antigen or the antibody (for example, IgG antibody) to trap the N antigen. Thus, the immunochromatographic test device in this case also has the problem in which whether the neutralizing antibody is produced by vaccination cannot be determined.

In such a situation, a test device and a test method for quickly and simply determining the efficacy of vaccination against a predetermined virus, for example, a novel coronavirus, or determining the history of vaccination inoculation (the presence or absence of the neutralizing antibody produced by natural infection) are not necessarily provided at a practical level, and practical application of the test device and the test method is desired.

In view of the aforementioned circumstances, it is an object of the present invention to provide a test device and a test method by immunochromatography that can quickly and simply determine the efficacy of vaccination against a predetermined virus, for example, a novel coronavirus, or determine the history of vaccination inoculation.

SUMMARY

The present invention involves a test device by immunochromatography including: a first test piece; a second test piece separate from the first test piece; and a case configured to integrally accommodate the first test piece and the second test piece. The case includes a dropping window on which a specimen is dropped, a first detection window through which a part of the first test piece can be visually observed from the outside, and a second detection window through which a part of the second test piece can be visually observed from the outside. The first test piece can detect the presence of a first antibody in the specimen, and the second test piece can detect the presence of a second antibody different from the first antibody in the specimen. A result from the first test piece visually observed through the first detection window and a result from the second test piece visually observed through the second detection window can be determined in parallel and at the same time.

The present invention also involves a test kit including the above-described test device, and a determination guide that allows for determining a state of a specimen including a possibility that an antibody is produced by vaccination on the basis of a test result from the first test piece and a test result from the second test piece.

The present invention also involves a test method using the above-described test device, the method including: a first test step of dropping the specimen on the first test piece to detect the presence or absence of the first antibody in the specimen; a second test step of dropping the specimen on the second test piece different from the first test piece to detect the presence or absence of the second antibody in the specimen; and a determination step of combining results from the first and second test steps to determine the state of the specimen.

The present invention also involves a test method for determining the presence or absence of a first antibody and a second antibody in a specimen by immunochromatography, where the first antibody is an antibody produced by vaccination or infection with a predetermined virus, and the second antibody is an antibody produced by infection with the virus. The method includes: dropping the specimen on a first test piece to determine the presence or absence of the first antibody in the specimen; dropping the specimen on a second test piece different from the first test piece to determine the presence or absence of the second antibody in the specimen; and combining a test result from the first test piece and a test result from the second test piece to determine whether the first antibody is produced by the vaccination in the specimen.

Advantageous Effects of Invention

According to the present invention can be provided a test device, a test kit, and a test method by immunochromatography that can quickly and simply determining the efficacy of vaccine against a predetermined virus, for example, a novel coronavirus.

DETAILED DESCRIPTION

Hereinafter, an embodiment of the present invention will be described with reference to the drawings. FIG. 1(A) to FIG. 4(H) are views illustrating examples of the present embodiment of the present invention. Portions assigned with the same reference numeral in the drawings indicate the same member. It is noted that in the drawings, some of the structures are appropriately omitted for the simplification of the drawings. The size, shape, thickness, and the like of members are appropriately exaggerated.

<Test device>

Figure 1A:
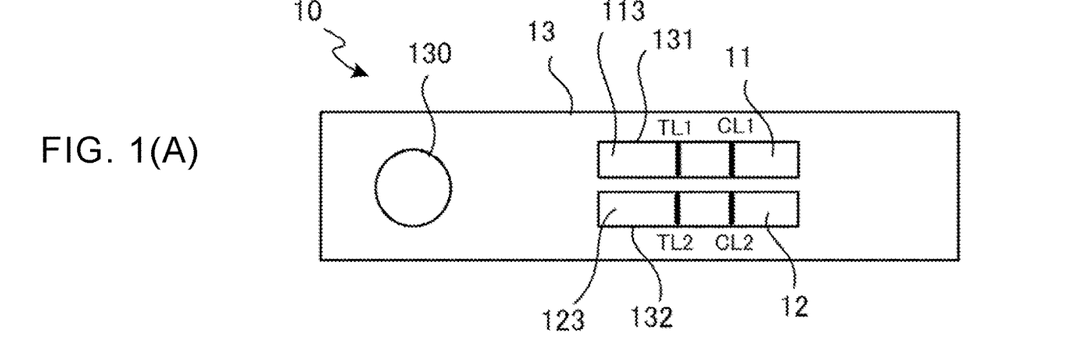
FIG. 1(A) is a plan view of a test device according to an embodiment of the present invention.
Figure 1B:
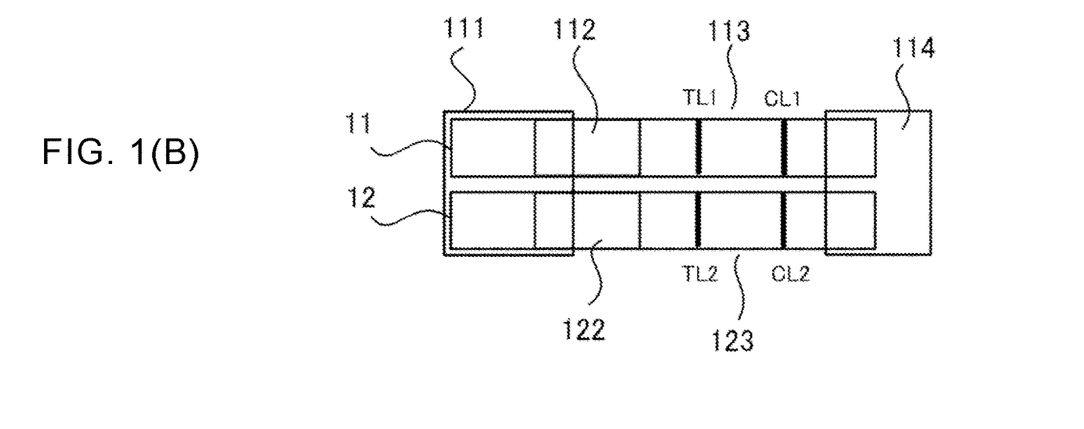
FIG. 1(B) is a plan view of a test piece.
Figure 1C:
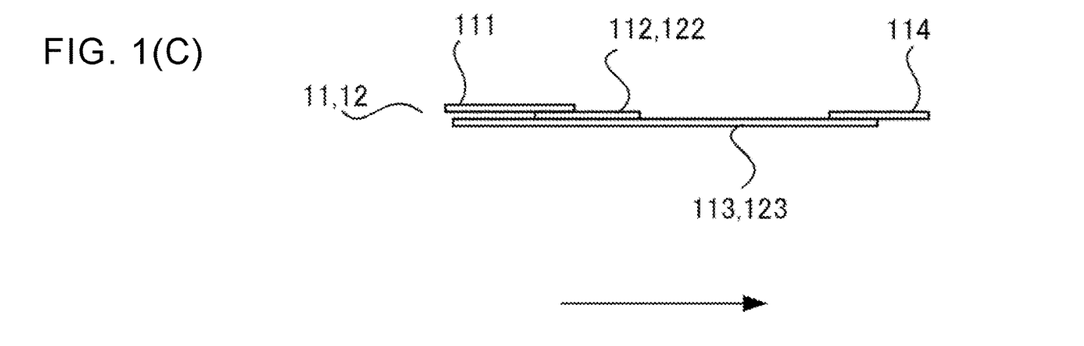
FIG. 1(C) is a cross-sectional side view of the test piece.

FIGS. 1(A)-1(C) include views illustrating a test device 10 according to the present embodiment. FIG. 1(A) is a plan view, FIG. 1(B) is an extracted plan view of an internal of the test device 10, and FIG. 1(C) is a cross-sectional side view of FIG. 1(B).

The test device 10 is a device for antibody test by immunochromatography. The test device 10 performs a reaction between an antibody in a specimen and a labeled body containing an antigen, causes the produced immune complex to migrate by capillary action, traps the immune complex with a previously immobilized antibody, and determines the presence or absence of a target antibody.

Specifically, as illustrated in FIG. 1(A), the test device 10 according to the present embodiment includes a first test piece 11, a second test piece 12, and a case 13.

The case 13 is, for example, an elongated rectangular box in plan view, and includes a dropping window 130 on which a specimen is dropped, a first detection window 131, and a second detection window 132. The first test piece 11 and the second test piece 12 are both band-like porous members (for example, cellulose membrane), and are integrally accommodated in the case 13 although they are provided as separate pieces. The first test piece 11 and the second test piece 12 are aligned so that a band lengthwise direction conforms to the lengthwise direction of the case 13 (in FIGS. 1(A)-1(C), a left-right direction). In this example, the first test piece 11 and the second test piece 12 are accommodated in the case 13 so that they are aligned (disposed in parallel) along the short-side direction (in FIGS. 1(A)-1(C), vertical direction) of the case 13.

The first detection window 131 is provided so that a part of the first test piece 11 can be visually observed from the outside. The second detection window 132 is provided so that a part of the second test piece 12 can be visually observed from the outside.

The first test piece 11 can detect the presence of a first antibody in the specimen to be dropped through the dropping window 130. The second test piece 12 can detect the presence of a second antibody in the same specimen as the specimen dropped on the first test piece 11 or in a specimen that is a sample of the same specimen and is dropped approximately simultaneously with dropping on the first test piece 11.

The test device 10 is configured to determine a detection result from the first test piece 11 visually observed through the first detection window 131 and a result from the second test piece 12 visually observed through the second detection window 132 in parallel and at the same time. More specifically, the test device 10 is configured such that the results from the first test piece 11 and from the second test piece 12 are visually observed in parallel and approximately at the same time, producing various types of determinations. Herein, the expressions "in parallel and at the same time" and "in parallel" mean that the test pieces 11 and 12 and the detection results thereof can be recognized collectively (at a glance without largely moving a line of sight), and are not limited to a case where the detection results of the test pieces 11 and 12 are obtained at an exactly simultaneous time, and to a case where the results of the test pieces 11 and 12 are disposed (aligned) in parallel.

The first antibody and the second antibody to be detected in the present embodiment are antibodies that are of the same type but trap different antigens. Specifically, the "first antibody" in the present embodiment is an immunoglobulin present only in human blood, and for example, is an antibody that binds to a part of a spike protein of a predetermined virus (for example, a SARS-CoV-2 virus). More specifically, the spike protein includes an S1 unit and an S2 unit, and the first antibody in the present embodiment is an antibody (for example, IgG antibody) that binds to (trap) a receptor-binding domain (RBD) in the S1 unit. Hereinafter, the spike protein is referred to as an "S antigen", a receptor-binding domain in the S1 unit (RBD portion extracted from the S1 unit) is referred to as an "S1/RBD antigen", and an IgG antibody (first antibody) that binds to the S1/RBD antigen is referred to as an "S1/RBD-IgG antibody".

The "second antibody" in the present embodiment is an immunoglobulin present only in human blood, and for example, is an antibody (for example, IgG antibody) that binds to (trap) a nucleocapsid protein of the predetermined virus (for example, a SARS-CoV-2 virus). Hereinafter, the nucleocapsid protein is referred to as an "NP antigen", and an IgG antibody (second antibody) that binds to the NP antigen is referred to as an "NP-IgG antibody".

As described above, the first antibody (S1/RBD-IgG antibody) and the second antibody (NP-IgG antibody) in the present embodiment are the same type of antibody (for example, IgG antibody) present in human blood, but trap different antigens. In this respect, the first antibody and the second antibody are different types of IgG antibodies.

Referring to FIGS. 1(B) and 1(C), the first test piece 11 is a member that includes a sample pad 111 to serve as a dropping portion on which the specimen is dropped, a first labeled body-containing portion 112 containing a first labeled body, a first detection portion 113, and an absorption pad 114 configured to absorb the dropped specimen. These constituents are connected so that their end portions superimpose each other in the band lengthwise direction. The specimen dropped on the sample pad 111 through the dropping window 130 migrates in the arrow direction toward the absorption pad 114 (in FIGS. 1(A)-1(C), from the left upstream to the right downstream). The "specimen" in the present embodiment is whole blood, serum, or plasma of human (subject), and may be a specimen liquid in which a developer is added thereto.

More specifically, the first labeled body-containing portion 112 is a conjugate pad containing an antigen (labeled antigen) and an antibody (labeled antibody) each labeled with colored particles such as gold nanoparticles. In this example, the labeled antigen in the first labeled body-containing portion 112 is an S1/RBD antigen capable of binding to the S1/RBD-IgG antibody (capable of trapping the S1/RBD-IgG antibody). The "first labeled body" in the present embodiment is a labeled antigen capable of binding to the S1/RBD-IgG antibody. In other words, this labeled antigen is an S1/RBD labeled antigen. The first labeled body binds to the S1/RBD-IgG antibody to form an immune complex (hereinafter referred to as a "first immune complex IC1") and migrates from the upstream side (in FIGS. 1(A)-1(C), left side) to the downstream side (in FIGS. 1(A)-1(C), right side). The labeled antibody in the first labeled body-containing portion 112 is a labeled antibody (labeled antibody LB1) of a non-human animal.

The first detection portion 113 is a membrane filter that is provided downstream of the first labeled body-containing portion 112. The first detection portion 113 includes a capture antibody line TL1 and a control antibody line CL1. In these antibody lines TL1 and CL1, the respective antibodies, a capture antibody T1 and a control antibody C1, for example, are linearly applied and immobilized in a width-wise direction of a band. The capture antibody T1 is an antibody derived from an animal and capable of trapping the first immune complex IC1. The control antibody C1 is an antibody capable of trapping a labeled antibody LB1 (an antibody not involved in the first immune complex IC1). The absorption pad 114 is provided downstream of the first detection portion 113.

The second test piece 12 is a member that includes the sample pad 111 to serve as a dropping portion on which the specimen is dropped, a second labeled body-containing portion 122 containing a second labeled body, a second detection portion 123, and the absorption pad 114 to absorb the dropped specimen. These constituents are connected so that their end portions superimpose each other in the band lengthwise direction. The second test piece 12 is separate from the first test piece 11, and is disposed in parallel but separately from the first test piece 11. In this example, the sample pad 111 and the absorption pad 114 are used both for the first test piece 11 and the second test piece 12. Specifically, the sample pad 111 is provided to be superimposed on the end portion (in this example, a left end portion) of each of both the first test piece 11 and the second test piece 12 in the band lengthwise direction, and the absorption pad 114 is provided to be superimposed on the other end portion (in this example, a right end portion) of each of both the first test piece 11 and the second test piece 12 in the band lengthwise direction. The specimen dropped on the sample pad 111 migrates in the arrow direction toward the absorption pad 114 (in FIGS. 1(A)-1(C), from the left upstream to the right downstream).

More specifically, the second labeled body-containing portion 122 is a conjugate pad containing an antigen (labeled antigen) and an antibody (labeled antibody) each labeled with colored particles such as gold nanoparticles. In this example, the labeled antigen in the second labeled body-containing portion 122 is an NP antigen capable of binding to the NP-IgG antibody (capable of trapping the NP-IgG antibody). The "second labeled body" in the present embodiment is a labeled antigen capable of binding to the NP-IgG antibody. In other words, this labeled antigen is an NP labeled antigen. The second labeled body binds to the NP-IgG antibody to form an immune complex (hereinafter referred to as a "second immune complex IC2") and migrates from the upstream side (in FIGS. 1(A)-1(C), left side) to the downstream side (in FIGS. 1(A)-1(C), right side). The labeled antibody in the second labeled body-containing portion 122 is a labeled antibody (labeled antibody LB2) of a non-human animal.

The second detection portion 123 is a membrane filter that is provided downstream of the second labeled body-containing portion 122. The second detection portion 123 includes a capture antibody line TL2 and a control antibody line CL2. In these antibody lines TL2 and CL2, the respective antibodies, a capture antibody T2 and a control antibody C2, for example, are linearly applied and immobilized in the widthwise direction of the band. The capture antibody T2 is an antibody derived from an animal and capable of trapping the second immune complex IC2. The capture antibody T2 may be the same antibody as the capture antibody T1 in the first detection portion 113.

The control antibody C2 is an antibody capable of trapping a labeled antibody LB2 (an antibody not involved in the second immune complex IC2).

The first test piece 11 is not limited to a laminated structure in which the sample pad 111, the conjugate pad (the first labeled body-containing portion) 112, the membrane filter (the first detection portion) 113, and the absorption pad 114 each partly superimpose each other as illustrated in FIG. 1(C). For example, the first test piece 11 may have a structure in which the sample pad 111, the conjugate pad 112, the membrane filter 113, and the absorption pad 114 are continuously disposed along the band lengthwise direction of a single band-like porous member so that their respective corresponding regions are adjacent to each other. The first test piece 11 may also have a structure in which only some of these constituents are laminated, or the like. In the following description, the first test piece 11 having the laminated structure as illustrated in FIG. 1(C) will be described as an example. However, when the first test piece 11 has a shape of a single band (or a band in which some of the constituents superimpose each other), the constituents described as the sample pad 111, the conjugate pad 112, the membrane filter 113, and the absorption pad 114 should be interpreted as regions corresponding to the respective constituents. For example, when "the sample pad 111" is described, it should be interpreted as "a region corresponding to the sample pad 111". The same is applied to the second test piece 12.

<Detection Principle of Test Device>

Figure 2:
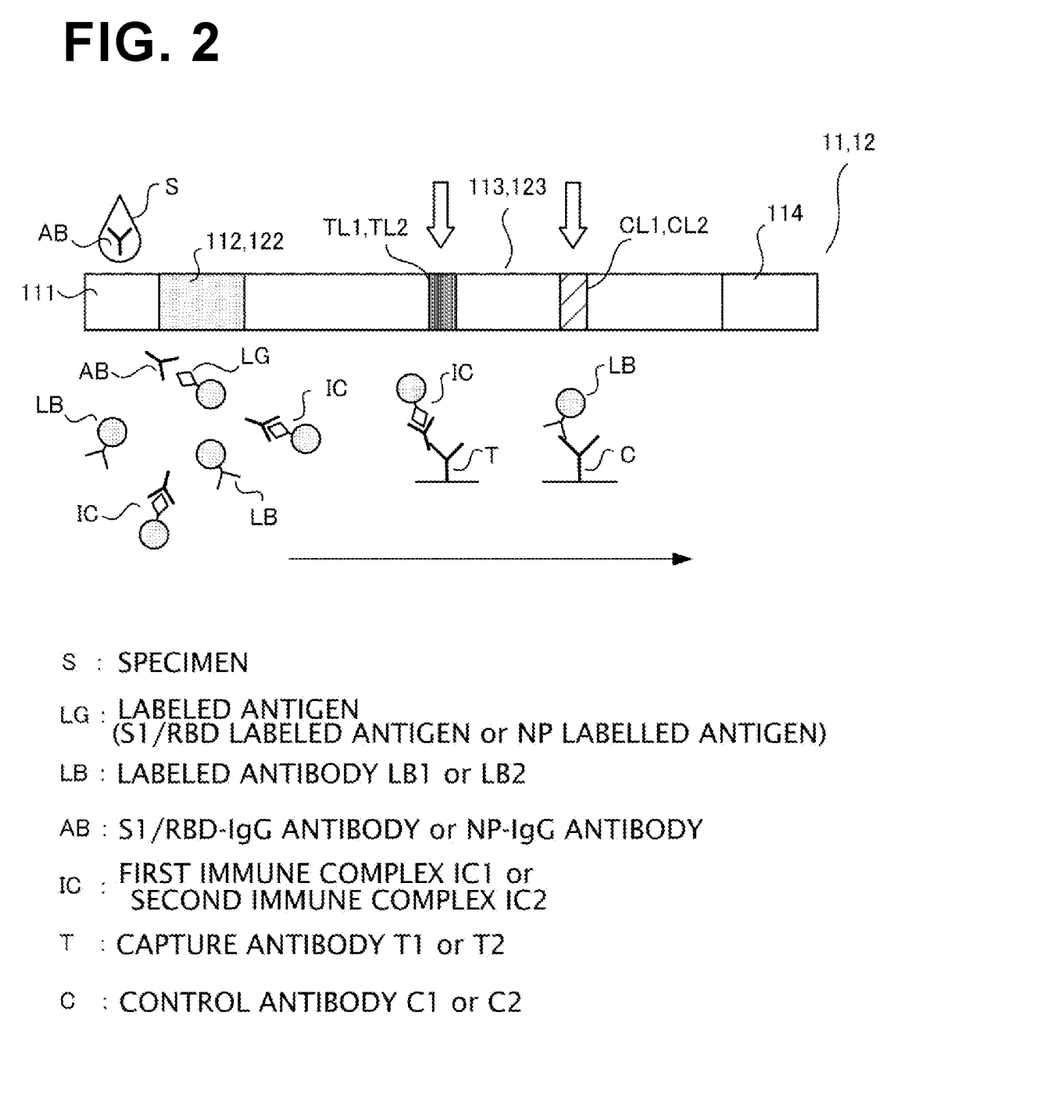
FIG. 2 is a schematic view illustrating the principles of test by immunochromatography.

Referring to FIG. 2, the detection principle of the test device 10 will be described. In the detection principle, the first test piece 11 is comparable with the second test piece 12, and thus antigens and antibodies of the first test piece 11 and the second test piece 12 are collectively illustrated in FIG. 2. Specifically, in FIG. 2, the labeled antigen (the S1/RBD labeled antigen and the NP labeled antigen) are collectively referred to as LG, the labeled antibodies (the labeled antibodies LB1 and LB2) are collectively referred to as LB, the antibodies (the S1/SBD-IgG antibody and the NP-IgG antibody) to be detected in the specimen are collectively referred to as AB, the first immune complex IC1 and the second immune complex IC2 are collectively referred to as IC, the capture antibodies T1 and T2 are collectively referred to as T, and the control antibodies C1 and C2 are collectively referred to as C.

When a specimen S is dropped through the dropping window 130 (not illustrated in FIG. 2), the specimen S permeates the first labeled body-containing portion 112 of the first test piece 11 and the second labeled body-containing portion 122 of the second test piece 12 through the sample pad 111 respectively (at approximately the same time) through the sample pad 111. Furthermore, the specimen S migrates to the downstream side through two routes via the first test piece 11 and the second test piece 12.

In the first test piece 11, the specimen migrates to the first detection portion 113 while dissolving the labeled antigen (the S1/RBD labeled antigen, and in FIG. 2, the labeled antigen LG) in the first labeled body-containing portion 112. When the specimen S contains the S1/RBD-IgG antibody to be tested (in FIG. 2, the antibody AB), the S1/RBD-IgG antibody (the antibody AB) binds to the S1/RBD labeled antigen (the labeled antigen LG) to form the first immune complex IC1 (in FIG. 2, the immune complex IC) and migrates downstream. The first immune complex IC1 (the immune complex IC) binds to the capture antibody T1 (in FIG. 2, the capture antibody T) in the capture antibody line TL1 and is trapped on the capture antibody line TL1. The trapping produces a state in which colored particles derived from the labeled antigen are concentrated on the capture antibody line TL1, and the capture antibody line TL1 is colored. The first detection window 131 is opened so that this coloring can be visually observed. When the colored state is visually observed, the presence or absence of the SI/RBD-IgG antibody in the specimen can be determined. In other words, when the capture antibody line TL1 is colored, it is determined that the specimen contains the S1/RBD-IgG antibody (positive).

When the specimen migrates, the labeled antibody LB1 (in FIG. 2, the labeled antibody LB) in the first labeled body-containing portion 112 also migrates downstream. The labeled antibody LB1 (the labeled antibody LB) does not bind to the S1/RBD labeled antigen (the labeled antigen LG) (without participation in the first immune complex IC1) and is not trapped on the capture antibody line TL1. However, the labeled antibody LB1 is trapped by the control antibody C1 (in FIG. 2, the control antibody C) immobilized downstream. This trapping produces a state in which colored particles derived from the labeled antibody LB1 are concentrated on the control antibody line CL1, and the control antibody line CL1 is colored. The first detection window 131 is opened so that this coloring can be visually observed. When the colored state is visually observed, it is confirmed that the specimen passed through the capture antibody line TL1 and reached the control antibody line CL1. In other words, when the capture antibody line TL1 is not colored and the control antibody line CL1 alone is colored, it is determined that the S1/RBD-IgG antibody is not present in the specimen (negative).

The second test piece 12 determines the presence or absence of the NP-IgG antibody in the same specimen as the specimen S that is tested by the first test piece 11. Since this principle is the same as that in the first test piece 11, a description will be partially omitted. The specimen migrates to the second detection portion 123 while dissolving the labeled antigen (the NP labeled antigen and the labeled antigen LG) in the second labeled body-containing portion 122. When the specimen contains the NP-IgG antibody to be tested (the antibody AB), the NP-IgG antibody binds to the NP labeled antigen (the labeled antigen LG) to form the second immune complex IC2 (the immune complex IC), and the second immune complex IC2 is trapped on the capture antibody line TL2. By this trapping, the capture antibody line TL2 is colored. The colored state can be visually observed through the second detection window 132. When the capture antibody line TL2 is colored, it is determined that the specimen contains the NP-IgG antibody (positive). In contrast, when the capture antibody line TL2 is not colored and the control antibody line CL2 alone is colored, it is determined that the NP-IgG antibody is not present (negative).

In the present embodiment, the specimen dropped through one dropping window 130 in the test device 10 is absorbed by the sample pad 111 of the first test piece 11 and the second test piece 12 approximately at the same time, and then migrates downstream through two routes via the test pieces 11 and 12. The first test piece 11 can determine the presence or absence of the S1/RBD-IgG antibody in the specimen. The second test piece 12 can determine the presence or absence of the NP-IgG antibody in the specimen.

Thus, the test device 10 according to the present embodiment can detect the presence or absence of two types of antibodies (the S1/RBD-IgG antibody and the NP-IgG antibody in the specimen) in parallel and at the same time by one test, where these antibodies are present in the same specimen and of the same type (for example, IgG antibody), and trap different antigens. This configuration can determine the state of the specimen by combining detection results of the two types of antibodies that trap different antigens contains in the same specimen. Thus, the test device 10 according to the present embodiment can be applied to various types of determinations including determining the efficacy of predetermined vaccination.

<Test Method>

Hereinafter, a method for testing an antibody according to the present embodiment will be described. A test method using the aforementioned test device 10 will be described. The test method includes a first test step of dropping the specimen on the first test piece 11 in the test device 10 to detect the presence or absence of the first antibody in the specimen, a second test step of dropping the specimen on the second test piece 12 in the test device 10 to detect the presence or absence of the second antibody in the specimen, and a determination step of combining results from the first test step and the second test step, that is, a detection state by the first detection portion 113 that can be visually observed through the first detection window 131 and a detection state by the second detection portion 123 that can be visually observed through the second detection window 132 to determine the state of the specimen. At the determination step, results of the presence or absence of the S1/RBD-IgG antibody and the presence or absence of the NP-IgG antibody in the specimen are combined to determine the final determination. Thus, one determination is derived from a plurality of determination candidates including a determination on a possibility that the antibody is produced by vaccination.

As described in the detection principle of the test device, when the specimen is dropped through the dropping window 130 in the test device 10, the first detection portion in the first test piece 11 detects the presence or absence of the S1/RBD-IgG antibody in the specimen. The S1/RBD-IgG antibody is an antibody (neutralizing antibody) to target a spike protein (S antigen) of the novel coronavirus. The second detection portion in the second test piece 12 detects the presence or absence of the NP-IgG antibody in the same specimen. In the present embodiment, the state of the specimen, specifically whether natural infection with the coronavirus has occurred and whether the neutralizing antibody is produced, is determined on the basis of the results.

However, when the presence or absence of the neutralizing antibody in the specimen can be detected by the test device 10, whether the neutralizing antibody is produced by viral infection or vaccination cannot be determined. The test method according to the present embodiment makes it possible to determine whether the detected S1/RBD-IgG antibody (neutralizing antibody) may have been produced by vaccination by combining the result from the first test piece 11 (the presence or absence of the S1/RBD-IgG antibody in the specimen) and the result from the second test piece 12 (the presence or absence of the NP-IgG antibody in the specimen).

Figure 3:
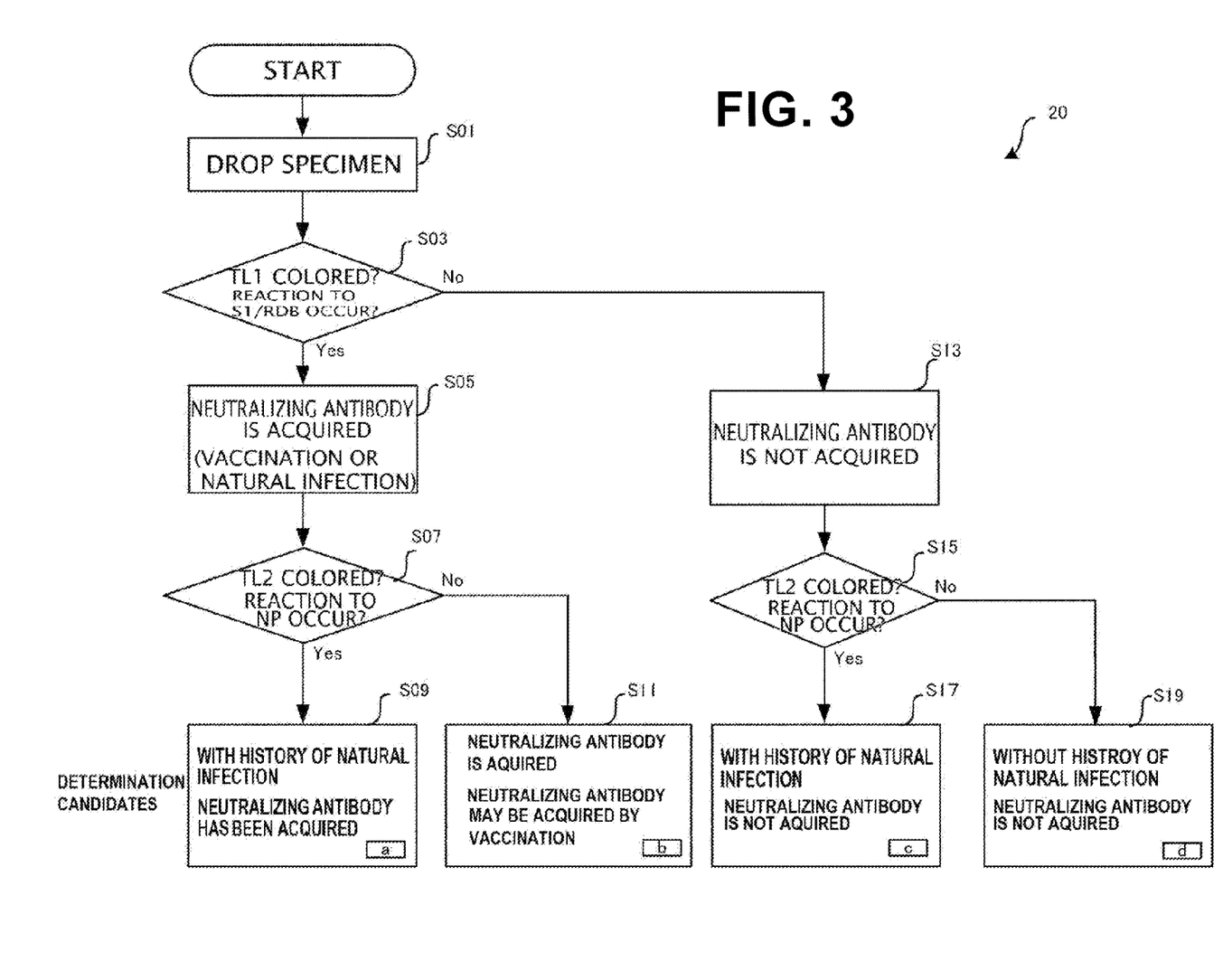
FIG. 3 is a flowchart illustrating an example of a test method according to the present embodiment.

Referring to FIG. 3 and FIGS. 4(A)-4(H), a description will be given of the test method according to the present embodiment, and a determination on whether the neutralizing antibody is acquired or the efficacy of vaccination (for example, a determination on a possibility that the neutralizing antibody has been produced by vaccination (a possibility that the detected S1/RBD-IgG antibody has been produced by vaccination)). FIG. 3 is a flowchart illustrating an example of the test method according to the present embodiment. FIGS. 4(A)-4(H) include plan views illustrating an outline of the test results of the first test piece 11 and the second test piece 12.

<<First Case>>

A determination in a first case using the test method according to the present embodiment will be described. The specimen is dropped on the test device 10 (Step S01), and the first detection window 131 in the first test piece 11 is visually observed to check the test result. When the capture antibody line TL1 is colored, that is, when the result is positive (Yes in Step S03), it is determined that the S1/RBD-IgG antibody (the neutralizing antibody) is present in the specimen (Step S05).

Subsequently, the second detection window 132 in the second test piece 12 detected in parallel and at the same time is visually observed to check the test result. When the capture antibody line TL2 is colored, that is, when the result is positive (Yes in Step S07), this means that the NP-IgG antibody is present (see FIG. 4(A)).

When the detection results of the first test piece 11 and the second test piece 12 are combined, the determination in the first case is that "subject has a history of natural viral infection, and neutralizing antibody is produced (acquired): determination a" (Step S09).

In the first case, the neutralizing antibody is acquired, but whether the neutralizing antibody is acquired by vaccination cannot be specified. However, when it is established that a subject is vaccinated before the test, a possibility that the neutralizing antibody is acquired by vaccination is also considered.

<<Second Case>>

Next, a determination in a second case will be described. When the capture antibody line TL1 of the first test piece 11 is colored, that is, when the result is positive (Yes in Step S03), it is determined that the S1/RBD-IgG antibody (the neutralizing antibody) is present (acquired). In this stage, however, it is not obvious whether the neutralizing antibody is produced (acquired) by vaccination or viral infection (natural infection).

Figure 4A:
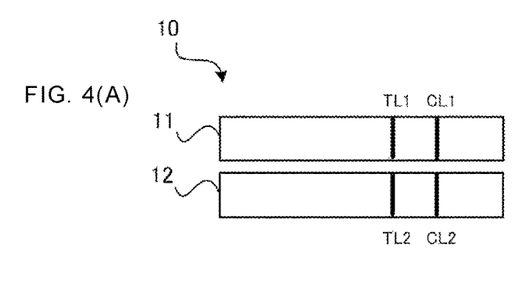
FIGS. 4(A)-4(H) are schematic views illustrating an example of the test method according to the present embodiment.
Figure 4B:
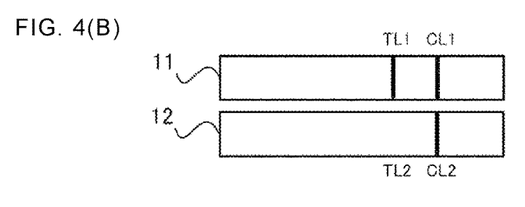
Figure 4C:
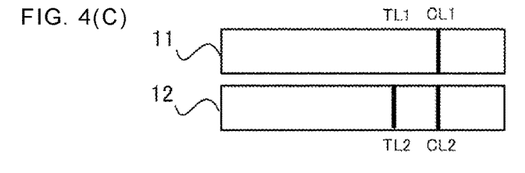
Figure 4D:
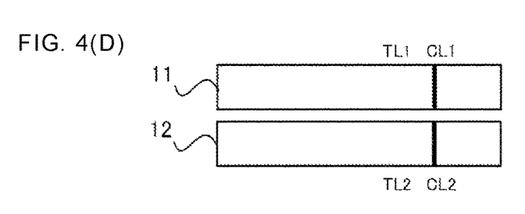

When the capture antibody line TL2 is not colored, that is, when the result is negative (No in Step S07), it is determined that the NP-IgG antibody is not present (see FIG. 4(B)).

In this case, from only the result that the NP-IgG antibody is not present, the possibility of natural viral infection can be determined to be low. Therefore, when it is not established that the subject is vaccinated, it is determined from the positive result in the first test piece 11 that the neutralizing antibody has been produced by natural infection. When it is established that the subject is vaccinated, the determination is that the neutralizing antibody has been produced by vaccination.

Like this, when the detection results of the first test piece 11 and the second test piece 12 are combined, the determination in the second case is that "neutralizing antibody is produced (acquired), and neutralizing antibody may be acquired by vaccination: determination b" (Step S11). Again, in this case, particularly, when it is established that the subject is vaccinated before the test, the possibility that the neutralizing antibody in the specimen is acquired by vaccination is higher, as described above.

<<Third Case>>

Next, a determination in a third case will be described. When the capture antibody line TL1 of the first test piece 11 is not colored, that is, when the result is negative (No in Step S03), it is determined that the S1/RBD-IgG antibody (neutralizing antibody) is not present (is not acquired) (Step S13). When the capture antibody line TL2 of the second test piece 12 is colored, that is, when the result is positive (Yes in Step S15), it is determined that the NP-IgG antibody is present (see FIG. 4(C)).

In this case, when the detection results of the first test piece 11 and the second test piece 12 are combined, the determination in the third case is that "subject has a history of natural viral infection, and neutralizing antibody is not produced: determination c" (Step S17). In the third case, for example, when it is established that the subject is vaccinated before the test, the determination is that the vaccination is not effective (has not been still effective).

<<Fourth Case>>

Next, a determination in a fourth case will be described. When the capture antibody line TL1 of the first test piece 11 is not colored, that is, when the result is negative (No in Step S03), it is determined that the S1/RBD-IgG antibody (neutralizing antibody) is not present (is not acquired). When the capture antibody line TL2 of the second test piece 12 is not colored, that is, when the result is negative (No in Step S15), it is determined that the NP-IgG antibody is not present (see FIG. 4(D)).

In this case, when the detection results of the first test piece 11 and the second test piece 12 are combined, the determination in the fourth case is that "subject has no history of natural viral infection, and neutralizing antibody is not produced: determination d" (Step S19). In the fourth case, for example, when it is established that the subject is vaccinated before the test, the determination is that the vaccination is not effective (has not been still effective).

Figure 4E:
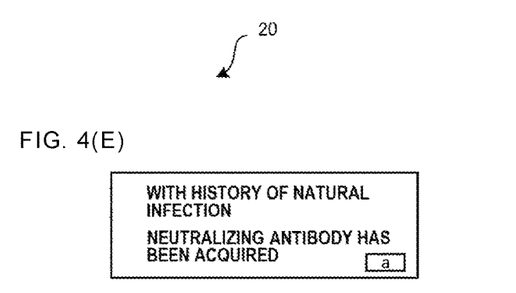
Figure 4F:
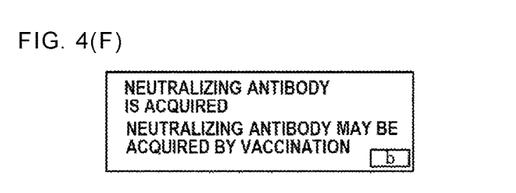
Figure 4G:
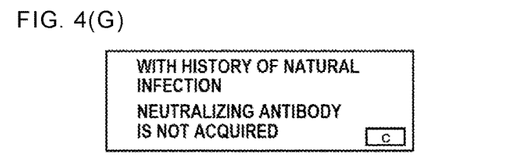
Figure 4H:
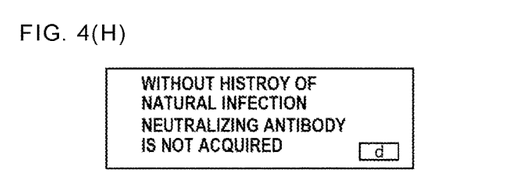

Thus, the test device 10 and the test method according to the present invention can derive one determination from a plurality of determination candidates including the efficacy of a predetermined vaccine (the determination a illustrated in Step S09 in FIG. 3 and in FIG. 4(E), the determination b illustrated in Step S11 in FIG. 3 and in FIG. 4(F), the determination c illustrated in Step S17 in FIG. 3 and in FIG. 4(G), and the determination d illustrated in Step S19 in FIG. 3 and in FIG. 4(G)). Therefore, a simple and quick method can test and determine the efficacy of a vaccine against a predetermined virus (for example, novel coronavirus), for example, a fact where the neutralizing antibody is not acquired although it is established that the subject is vaccinated (the third case and the fourth case), or when the neutralizing antibody is present in the specimen, whether the neutralizing antibody is produced by natural viral infection or vaccination (the second case) or the like.

The test method according to the present embodiment makes various determinations of the antibodies by the following processes. In this case, the test method is not limited to a method using the test device 10.

Specifically, the method is a test method for determining the presence or absence of a first antibody and a second antibody in the specimen by immunochromatography where the first antibody is an antibody produced by vaccination or infection with a predetermined virus, and the second antibody is an antibody produced by infection with the virus. Then, the method includes: dropping the specimen on the first test piece 11 to determine the presence or absence of the first antibody in the specimen, dropping the same specimen on the second test piece 12 different from the first test piece 11 to determine the presence or absence of the second antibody in the specimen, and combining a test result from the first test piece 11 and a test result from the second test piece 12 to derive a determination from determination candidates including the possibility that the first antibody is produced in the specimen by vaccination.

In this case, particularly, when the test result from the first test piece 11 is positive and the test result from the second test piece 12 is negative, it is determined that there is a possibility that the first antibody may have been produced in the specimen by the vaccination.

<Test Kit>

Next, a test kit 30 according to the present embodiment will be described with reference to FIGS. 5(A) and 5(B). The test kit 30 according to the present embodiment includes the test device 10 and a determination guide 20. The determination guide 20 allows the user to determine the state of the specimen including a possibility that the antibody is produced by predetermined vaccination on the basis of the test result from the first test piece 11 and the test result from the second test piece 12.

Figure 5A:
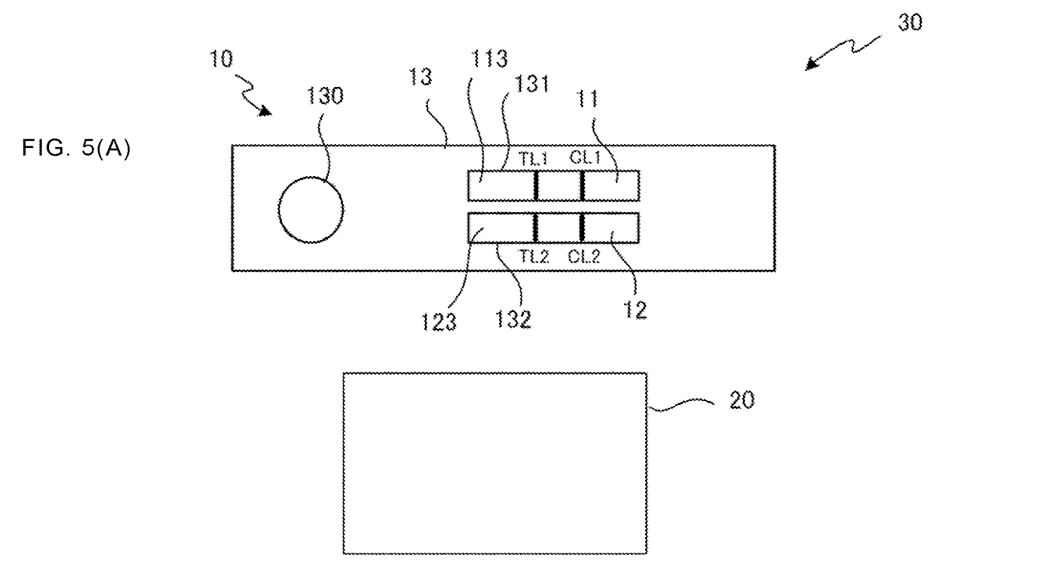
FIGS. 5(A) and 5(B) are schematic views illustrating an example of a test kit according to the present embodiment.
Figure 5B:
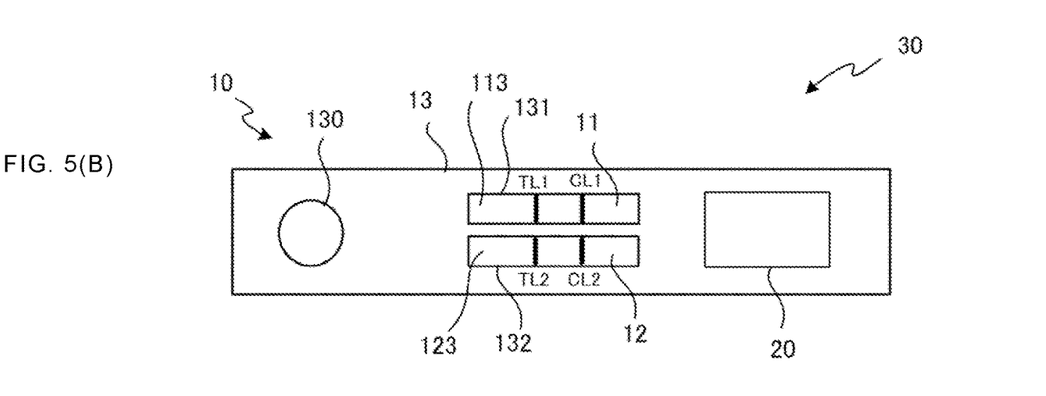

The determination guide 20 may be a printed matter separate from the test device 10, such as paper, as illustrated in FIG. 5(A), or may be a guide that is displayed (printed) directly on the test device 10 as illustrated in FIG. 5(B). For example, when the determination guide 20 is paper, a flowchart as illustrated in FIG. 3 may be printed on paper. Sets of the test results of the first test piece 11 and the second test piece 12 as illustrated in FIGS. 4(A)-4(H), that is, the colored state (schematic view) (FIGS. 4(A) to 4(D)), and determinations based on the colored states (FIGS. 4(E) to 4(H), the determinations a to d) may be printed.

The determination guide 20 may be provided, for example, in a form of an application of a smartphone, a personal computer, or the like although the illustration thereof is omitted. In this case, when the application is initiated, for example, questions as illustrated in the flowchart in FIG. 3 are successively displayed. When answers are input in accordance with the display, any one of the determinations a to d may be displayed. Furthermore, when the application is initiated, a set of the colored states (schematic views) of the first test piece 11 and the second test piece 12 and the determination based on the colored states (any of the determinations a to d) may be displayed. Alternatively, the application may be configured so that when the application is initiated, the application is shifted to a photographing mode or the like. When the actual test results of the first test piece 11 and the second test piece 12 are photographed and sent, any one of the determinations a to d illustrated in FIGS. 4(E) to 4(H) may be displayed.

The determination guide 20 is not limited to the aforementioned examples and may be in any form as long as an examiner can uniquely acquire the state of the specimen (specifically, any of the determinations a to d illustrated in FIGS. 4(E) to 4(H)) including a possibility that the antibody is produced by predetermined vaccination based on the test results of the first test piece 11 and the second test piece 12.

Figure 6:
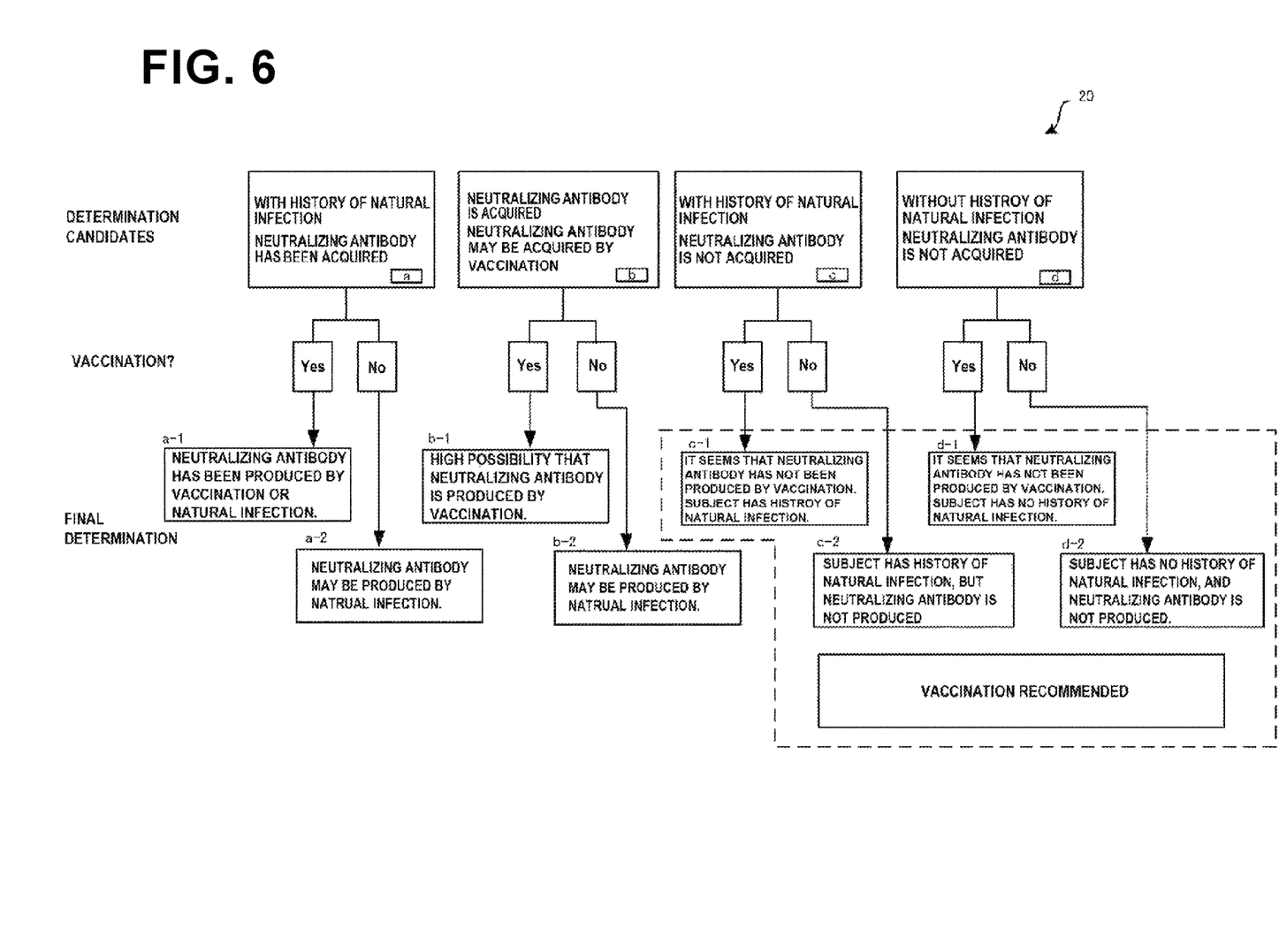
FIG. 6 is a schematic view illustrating an example of the test kit according to the present embodiment.

FIG. 6 is a view illustrating another example of the determination guide 20. The aforementioned determinations a to d are determinations in a stage where the presence or absence of vaccination in the subject is not (cannot be) specified. However, the determination guide 20 in this example illustrated in FIG. 6 makes a more detailed determinations possible on the basis of the aforementioned determinations a to d and the presence or absence of vaccination in the subject (a fact that the subject is vaccinated).

Specifically, when the determination a is given and when it is established that the subject is vaccinated, the determination is that "neutralizing antibody has been produced by vaccination or natural infection". To a user of the test kit 30, for example, "Neutralizing antibody has been produced by vaccination or natural infection (determination a-1)" or the like is displayed.

When the determination a is given and when it is not established that the subject is vaccinated, the determination is that "neutralizing antibody has been produced by natural infection". To the user, for example, "Neutralizing antibody may be produced by natural infection (Determination a-2)" or the like is displayed.

When the determination b is given and when it is established that the subject is vaccinated, it is determined that "there is a high possibility that neutralizing antibody is produced by vaccination (since the result from the second test piece 12 is negative)". To the user, for example, "There is a high possibility that neutralizing antibody is produced by vaccination (Determination b-1)" or the like is displayed.

When the determination b is given and when it is established that the subject is vaccinated, it is determined that "there is a possibility that neutralizing antibody may be produced by natural infection (since the result from the first test piece 11 is positive)". To the user, for example, "there is a possibility that neutralizing antibody may be produced by natural infection (Determination b-2)" or the like is displayed.

When the determination c is given and when it is established that the subject is vaccinated, it is determined that "there is a high possibility that neutralizing antibody is not produced although subject is vaccinated. Although subject has a history of natural infection, neutralizing antibody is not produced by the natural infection". To the user, for example, "It seems that neutralizing antibody has not been produced (by vaccination), but subject has a history of natural infection (Determination c-1)" or the like is displayed.

When the determination c is given and when it is not established that the subject is vaccinated, it is determined that "subject has a history of natural infection but neutralizing antibody is not produced (by natural infection)". To the user, for example, "Subject has a history of natural infection, but neutralizing antibody is not produced (Determination c-2)" or the like is displayed.

When the determination d is given and when it is established that the subject is vaccinated, it is determined that "There is a high possibility that neutralizing antibody is not produced although the subject is vaccinated. Subject has no history of natural infection". To the user, for example, "It seems that neutralizing antibody has not been produced by vaccination. Subject has no history of natural infection (Determination d-1)" or the like is displayed.

When the determination d is given and when it is not established that the subject is vaccinated, it is determined that "subject has no history of natural infection, and neutralizing antibody is not produced". To the user, for example, "subject has no history of natural infection and neutralizing antibody is not produced (Determination d-2)" or the like is displayed. For example, to a subject who does not acquire the neutralizing antibody, a recommendation such as that "Vaccination recommended" or the like may be displayed.

The flow of determination illustrated in FIG. 6 may be displayed, for example, after the flowchart (Steps S09, S11, S17 and S19) illustrated in FIG. 3 that is the determination guide 20. For example, following the results of determinations illustrated in FIGS. 4(A)-4(H), which is the determination guide 20, the user may be allowed to select the presence or absence of vaccination to derive the final determinations a-1 to d-2 illustrated in FIG. 6. The final determinations a-1 to d-2 illustrated in FIG. 6 may be derived by the application or the like.

When the determination guide 20 as illustrated in FIG. 6 is used, the user obtains the final determinations a-1 to d-2. Thus, the state of the subject can be simply and uniquely ascertained.

An example of the present embodiment of the present invention have been described above, but the present invention is not limited to the example.

For example, one test device 10 may include a plurality of dropping windows 130. Specifically, the dropping window 130 may be provided in each of both the first test piece 11 and the second test piece 12, and the same specimen may be dropped through each of the dropping windows 130.

An example in which the first test piece 11 and the second test piece 12 are disposed in parallel along the short-side direction of the case 13 has been described, and the present invention is not limited to this example. The first test piece 11 and the second test piece 12 may be aligned linearly (separate from each other) along the lengthwise direction of the case 13. However, when the test pieces 11 and 12 are aligned linearly, it is possible that the colored states of the test pieces may be more difficult to be visually observed. Furthermore, it is necessary to drop the specimen twice. When the test pieces 11 and 12 are disposed in parallel, the colored states of the test pieces are likely to be collectively recognized as a pattern, for example, as illustrated in FIGS. 4(A)-4(H), and easily compared with the determination guide 20 and the like. The sample pad 111 can be shared by the first test piece 11 and the second test piece 12 as illustrated in FIGS. 1(A)-1(C), and the specimen can be supplied to the first test piece 11 and the second test piece 12 by one procedural step of dropping the specimen.

In the present embodiment, a case where the antibody to be detected is an IgG antibody has been described. However, the antibody to be detected may be an IgM antibody or other immunoglobulins.

A configuration of the sample pad 111 and the absorption pad 114 is not limited to the configuration in which the sample pad 111 and the absorption pad 114 are used for both the first test piece 11 and the second test piece 12. The sample pad 111 and the absorption pad 114 may be provided separately in each of both the first test piece 11 and the second test piece 12.

The labeled antibody LB1 in the first labeled body-containing portion 112, the labeled antibody LB2 in the second labeled body-containing portion 122, and the control antibodies C1 and C2 may be different antibodies, or at least one set of the antibodies among these may be the same antibodies.

It should be noted that the test device 10 of the present invention is not limited to the above-described embodiment and can be modified in various manner without departing from the scope of the present invention.

The invention claimed is:

1. A test kit comprising:
   an immunochromatography test device; and
   a determination guide,
   wherein the test device comprises a case that includes a dropping window on which a specimen is dropped, a detection window, and a test piece accommodated in the case, wherein
   the test piece includes:
      a first test piece comprising a first detection portion,
      a second test piece comprising a second detection portion, and
      a dropping area common to the first test piece and the second test piece;
   wherein the test device is configured so that
      the first test piece and second test piece are aligned in parallel such that a band lengthwise direction conforms to a lengthwise direction of the test device and, when the specimen is dropped on the dropping area through the dropping window, the specimen is caused to migrate downstream and the same specimen is allowed to reach both the first detection portion and the second detection portion;
      the first detection portion can trap a complex of a first labeled body and a first antibody contained in the specimen;
      the second detection portion can trap a complex of a second labeled body and a second antibody contained in the specimen;
      the first antibody is an antibody that is produced by vaccination or infection with a predetermined virus and that binds to a part of a spike protein;
      the second antibody is an antibody that is produced by infection with the virus that binds to a part of a nucleocapsid protein; and
      the test device is configured so that a test result from the first detection portion for the specimen dropped onto the dropping area and a test result from the second detection portion for the same specimen, both visually observed through the detection window, can be determined in parallel and at the same time,
   wherein the test device distinguishes a single state from among multiple states, wherein the single state is selected from the group consisting of:
      a first state wherein a positive test result is observed in both the first detection portion and the second detection portion, which indicates a history of natural virus infection and that a neutralizing antibody has been produced,
      a second state wherein a positive test result is observed only in the first detection portion, which indicates that a neutralizing antibody has been produced,
      a third state, wherein a positive test result is observed only in the second detection portion, which indicates that a neutralizing antibody has not been produced, and
      a fourth state, wherein a positive test result is not observed in both the first detection portion and the second detection portion, which indicates that a neutralizing antibody has not been produced,
   wherein the determination guide allows for determining whether the specimen dropped onto the dropping area conforms to the first state, the second state, the third state, or the fourth state,
   the determination guide is provided on the case,
   the dropping window, the detection window, and the determination quide are arranged at a surface of the case along the lengthwise direction of the test device, and
   the determination guide is provided directly adjacent to the detection window.

2. The test kit according to claim 1, wherein a number of the dropping window is one.

3. The test kit according to claim 1, wherein the first antibody and the second antibody are antibodies that are derived from human and same type of immunoglobulin and trap different antigens.

4. The test kit according to claim 1, comprising a first labelled body-containing portion containing the first labeled body, and a second labeled body-containing portion containing the second labeled body.

5. The test kit according to claim 1, wherein:
   the first labeled body includes, as an antigen, a part of a spike protein of the virus; and
   the second labeled body includes, as an antigen, a nucleocapsid protein of the virus.

6. The test kit according to claim 1, wherein the virus is a SARS-COV-2 virus.

7. The test kit according to claim 1, wherein the determination guide is directly printed on the surface of the case of the test device.

* * * * *